(12) United States Patent
Trivett et al.

(10) Patent No.: US 10,438,786 B2
(45) Date of Patent: Oct. 8, 2019

(54) PROBE ASSEMBLY CONNECTOR

(71) Applicant: Micromass UK Limited, Wilmslow, Cheshire (GB)

(72) Inventors: Ian Trivett, Cheadle (GB); Stephen O'Brien, Manchester (GB); David Gordon, Middlewich (GB)

(73) Assignee: MICROMASS UK LIMITED, Wilmslow (GB)

( * ) Notice: Subject to any disclaimer, the term of this patent is extended or adjusted under 35 U.S.C. 154(b) by 136 days.

(21) Appl. No.: 15/465,070

(22) Filed: Mar. 21, 2017

(65) Prior Publication Data

US 2017/0292641 A1 Oct. 12, 2017

(30) Foreign Application Priority Data

Apr. 11, 2016 (GB) .................................. 1606123.6
Apr. 11, 2016 (GB) .................................. 1606124.4

(51) Int. Cl.
*F16L 15/08* (2006.01)
*G01N 30/72* (2006.01)
(Continued)

(52) U.S. Cl.
CPC .......... *H01J 49/0404* (2013.01); *F16L 15/08* (2013.01); *G01N 30/7233* (2013.01);
(Continued)

(58) Field of Classification Search
CPC ......... F16L 15/08; F16L 27/12; F16L 37/505; H01J 49/0404; H01J 49/0422;
(Continued)

(56) References Cited

U.S. PATENT DOCUMENTS

| 4,641,541 A | 2/1987 | Sharp |
| 4,991,883 A * | 2/1991 | Worden .................. B01J 4/001 285/334.4 |

(Continued)

FOREIGN PATENT DOCUMENTS

| JP | 2009294086 | 12/2009 | |
| WO | WO-8906766 A1 * | 7/1989 | ............ F16L 37/121 |

OTHER PUBLICATIONS

Herring et al., "*An On-Line Preconcentrator and the Evaluation of Electrospray Interfaces for the Capillary Electrophoresis/Mass Spectrometry of Peptides*", Rapid Communications in Mass Spectrometry, vol. 13, No. 1, pp. 1-7, 1999.
(Continued)

*Primary Examiner* — James M Hewitt, II
*Assistant Examiner* — Stacy N Lawson
(74) *Attorney, Agent, or Firm* — Womble Bond Dickinson (US) LLP; Deborah M. Vernon; Heath T. Misley

(57) ABSTRACT

An attachment device for releasably attaching a fluid line to a fluid inlet or outlet is disclosed. The device comprises an attachment member for releasably engaging a fluid inlet or outlet, and an elastic member coupled to the attachment member. The attachment device is attachable to a fluid line such that the attachment member is moveable relative to the fluid line and such that movement of the attachment member relative to the fluid line causes elastic deformation of the elastic member.

13 Claims, 8 Drawing Sheets

(51) Int. Cl.
*H01J 49/04* (2006.01)
*G01N 27/62* (2006.01)

(52) U.S. Cl.
CPC ........ *H01J 49/0422* (2013.01); *G01N 27/622* (2013.01); *G01N 30/7266* (2013.01)

(58) Field of Classification Search
CPC ........... G01N 30/7233; G01N 30/7266; G01N 30/7206; G01N 30/6026; G01N 30/6039; G01N 27/622
See application file for complete search history.

(56) References Cited

U.S. PATENT DOCUMENTS

| | | | |
|---|---|---|---|
| 5,163,722 A * | 11/1992 | Worden | F16L 37/242 285/101 |
| 5,175,433 A | 12/1992 | Browner et al. | |
| 5,234,235 A * | 8/1993 | Worden | F16L 29/04 285/334.4 |
| 6,193,286 B1 * | 2/2001 | Jones | G01N 30/6004 285/343 |
| 6,753,521 B1 | 6/2004 | Park et al. | |
| 7,075,066 B2 | 7/2006 | Bailey et al. | |
| 7,960,711 B1 | 6/2011 | Sheehan et al. | |
| 8,227,750 B1 | 7/2012 | Zhu et al. | |
| 8,384,026 B2 | 2/2013 | O'Malley et al. | |
| 8,723,109 B2 | 5/2014 | Newton | |
| 8,759,758 B2 | 6/2014 | Steiner et al. | |
| 9,188,569 B2 | 11/2015 | Graham | |
| 9,459,240 B2 | 10/2016 | Vorm | |
| 2005/0061673 A1 | 3/2005 | Presto Elgstoen et al. | |
| 2014/0305801 A1 | 10/2014 | Peterson et al. | |
| 2015/0090595 A1 * | 4/2015 | Lueth | G01N 30/6026 204/605 |
| 2015/0145246 A1 * | 5/2015 | Pa | B01L 3/563 285/332 |
| 2015/0209787 A1 * | 7/2015 | Brann | G01N 30/461 29/469 |
| 2015/0285414 A1 * | 10/2015 | Tomida | G01N 30/6039 285/389 |
| 2015/0323509 A1 * | 11/2015 | Kirby | G01N 30/30 210/175 |
| 2015/0369402 A1 * | 12/2015 | Pa | F16L 49/06 285/386 |
| 2016/0217992 A1 | 7/2016 | O'Brien et al. | |

OTHER PUBLICATIONS

Jackson et al., "*Electrical Equivalence of Electrospray Ionization with Conducting and Nonconducting Needles*", Analytical Chemistry, vol. 71, No. 17, pp. 3777-3784, 1999.

Kertesz et al., "*Minimizing Analyte Electrolysis in an Electrospray Emitter*", Journal of Mass Spectrometry, vol. 36, No. 2, pp. 204-210, 2001.

* cited by examiner

PROBE ASSEMBLY CONNECTOR

CROSS-REFERENCE TO RELATED APPLICATIONS

This application claims priority from and the benefit of United Kingdom patent application No. 1606124.4 filed on 11 Apr. 2016, and United Kingdom patent application No. 1606123.6 filed on 11 Apr. 2016. The entire content of these applications is incorporated herein by reference.

FIELD OF THE INVENTION

This invention relates generally to mass and/or ion mobility spectrometers, and in particular to apparatus for coupling liquid chromatography systems with mass and/or ion mobility spectrometers.

BACKGROUND

Liquid chromatography systems are an important tool to the analytical chemist for the separation and analysis of samples of interest. Often, after separation in the liquid chromatograph, the components require further analysis to confirm the identity of these components. This may be performed using a mass and/or ion mobility spectrometer. However, connecting liquid chromatography systems to mass and/or ion mobility spectrometers can be a difficult and time consuming task.

Typically tubing is provided for delivering eluent from the liquid chromatography system to an ion source of the mass and/or ion mobility spectrometer. However, if the attachment between the tubing and the liquid chromatography system and/or between the tubing and the mass and/or ion mobility spectrometer is not formed correctly, a dead volume may form and eluent may leak.

A dead volume can have a detrimental impact on the quality of the chromatography, and can increase the likelihood of eluent leaking. The presence of liquid eluent in the vicinity of a mass and/or ion mobility spectrometer can be hazardous to a user, may give rise to the risk of electrical shock, and can give rise to poor performance and/or poor data.

It is therefore desired to provide improved apparatus for mass and/or ion mobility spectrometry.

SUMMARY

According to an aspect there is provided an attachment device for releasably attaching a fluid line to a fluid inlet or outlet, the device comprising:

an attachment member for releasably engaging a fluid inlet or outlet; and an elastic member coupled to the attachment member;

wherein the attachment device is attachable to a fluid line such that the attachment member is moveable relative to the fluid line and such that movement of the attachment member relative to the fluid line causes elastic deformation of the elastic member.

Various embodiments are directed to an attachment device for releasably attaching a fluid line to a fluid inlet or outlet. The attachment device comprises an attachment member, e.g. an attachment fitting for releasably engaging a complementary fitting on a fluid inlet or outlet, and an elastic member coupled to the attachment member. The attachment device is attachable to a fluid line such that movement of the attachment member relative to the fluid line causes elastic deformation of the elastic member, i.e. the attachment device is "spring loaded".

According to various embodiments, when the attachment device is used to releasably attach a fluid line to a fluid inlet or outlet, the elastic member is elastically deformed, e.g. so as to exert a force that acts to force and/or maintain the fluid line in contact with the fluid inlet or outlet. This prevents the formation of dead volumes, even if, for example, the attachment device is incorrectly attached to the fluid inlet or outlet, and reduces the likelihood of leaking. This also allows the attachment device and/or the fluid line to which it is attached to be used in respect of multiple different fluid inlet or outlet devices.

It will be appreciated, therefore, that various embodiments provide improved apparatus for mass and/or ion mobility spectrometry.

The attachment device may be configured such that when the attachment device is attached to a fluid line, the attachment member is moveable relative to the fluid line, and movement of the attachment member relative to the fluid line causes elastic deformation of the elastic member.

The attachment device may be attachable to a fluid line such that the distance between the attachment member and an outlet and/or inlet of the fluid line is variable and such that variation of the distance causes elastic deformation of the elastic member.

The attachment device may be configured such that when the attachment device is attached to a fluid line, the distance between the attachment member and an outlet and/or inlet of the fluid line is variable, and variation of the distance causes elastic deformation of the elastic member.

The elastic member may comprise a helical tension spring.

The attachment device may be attachable to a fluid line such that an end or other portion of the elastic member is fixed with respect to the fluid line.

The attachment device may be configured such that when the attachment device is attached to a fluid line, an end or other portion of the elastic member is fixed with respect to the fluid line.

The fluid line may comprise a first rigid member attached to the outlet and/or inlet of the fluid line.

The attachment device may be attachable to a fluid line such that an end or other portion of the elastic member is connected to the first rigid member.

The attachment device may be configured such that when the attachment device is attached to a fluid line, an end or other portion of the elastic member is connected to the first rigid member.

The attachment device may comprise a second rigid member coupled to the elastic member.

The elastic member may comprise a first portion having a first diameter and a second portion having a second larger diameter; and the first diameter may be less than or equal to an internal diameter of the second rigid member, and the second diameter may be greater than the internal diameter of the second rigid member.

The attachment member may be attached to the second rigid member, e.g. fixedly attached to the second rigid member.

The attachment member second rigid member a screw threaded portion and/or ratchet mechanism for engaging a complementary profile on the fluid inlet or outlet so as to releasably secure the fluid line to the fluid inlet or outlet.

According to an aspect there is provided apparatus for releasably attaching a fluid line to a fluid inlet or outlet, the apparatus comprising:

an attachment device as described above; and a fluid line;

wherein the attachment device is attached to the fluid line such that the attachment member is moveable relative to the fluid line and such that movement of the attachment member relative to the fluid line causes elastic deformation of the elastic member.

The attachment device may be attached to the fluid line such that the distance between the attachment member and the outlet and/or inlet of the fluid line is variable, and variation of the distance causes elastic deformation of the elastic member.

The attachment device may be attached to the fluid line such that an end or other portion of the elastic member is fixed with respect to the fluid line.

The fluid line may comprise a first rigid member attached to the outlet and/or inlet of the fluid line.

The attachment device may be attached to the fluid line such that an end or other portion of the elastic member is connected to the first rigid member.

The fluid line may comprise a device or marking positioned on the fluid line such that at least a portion of the device or marking is exposed when the attachment device is correctly or fully releasably attached to the fluid inlet or outlet.

According to an aspect there is provided apparatus comprising:

apparatus as described above; and a fluid inlet or outlet, wherein the attachment device is releasably attachable to the fluid inlet or outlet so as to releasably attach the fluid line to the fluid inlet or outlet.

The apparatus may comprise:

a device fitted to the fluid line, wherein the device is configured to intercept liquid on the fluid line and to cause at least some of the intercepted liquid to drip or otherwise fall from the device and/or from the fluid line.

The device may comprise a first (e.g. tubular) portion and a conical portion.

According to an aspect there is provided a device for intercepting liquid on a member, the device comprising:

a first portion; and a conical portion;

wherein the device is configured to be fitted to a member; and wherein the device is configured to intercept liquid on a member to which it is fitted, and to cause at least some of the intercepted liquid to drip or otherwise fall from the device and/or from the member.

The device may be configured such that when the device is fitted to a member, most or all of the conical portion is spaced apart from the member.

The device may be configured such that when the device is fitted to a member, the device can move and/or rotate relative to the member.

The conical portion may be configured to be collapsible.

The conical portion may comprise one or more slots or other indentations.

According to an aspect there is provided apparatus comprising:

a first member; and a device as described above;

wherein the attachment device is fitted to the member; and wherein the device is configured to intercept liquid on the member, and to cause at least some of the intercepted liquid to drip or otherwise fall from the device and/or from the member.

The device may be fitted to the member, such that most or all of the conical portion is spaced apart from the member.

The device may be fitted to the member, such that the device can move and/or rotate relative to the member.

The member may comprise a line, wire, cable, tube, pipe or other member.

According to an aspect there is provided a method comprising:

providing apparatus as described above;

using the attachment device to releasably attach the fluid line to a fluid inlet or outlet; and delivering fluid from the fluid outlet to the fluid line; or delivering fluid from the fluid line to the fluid inlet.

According to an aspect there is provided a method comprising:

providing a device as described above;

fitting the device to a member; and delivering liquid to the member.

The fluid line may optionally form part of a probe assembly.

The probe assembly may comprise:

an inlet for receiving an eluent from a chromatography device;

an outlet for delivering the eluent to an ion source of a mass and/or ion mobility spectrometer; and an outlet attachment device for attaching the outlet to the apparatus.

The outlet may comprise a capillary and optionally an electrically conductive member surrounding at least part of the capillary.

The fluid line may comprise a fluid line for transporting eluent from the inlet to the capillary, and the probe may further comprise a joint between the fluid line and the capillary, wherein the joint is downstream of the outlet attachment device.

The electrically conductive member may be arranged to receive a voltage upon connection of the outlet attachment device to the spectrometer and the electrically conductive member may be arranged to be in electrical connection with the capillary.

The outlet of the probe assembly may be configured to be insertable into an orifice of the spectrometer and the outlet attachment device may be configured so as to releasably engage the orifice so as to releasably attach the probe to the spectrometer.

The joint may be arranged in the probe so as to be downstream of the orifice (i.e. within the spectrometer) when the outlet attachment device is connected to the spectrometer.

It will be appreciated that the term "downstream" used herein refers to the direction from the inlet end to the outlet end of the fluid line and/or probe assembly.

The capillary may be configured to spray eluent from its outlet.

The capillary may be configured so as to transmit the voltage to the eluent being sprayed therefrom for forming charged droplets of eluent.

The capillary may be an electrospray capillary, an atmospheric pressure chemical ionisation capillary or similar.

The inlet for receiving the eluent may be spaced from the outlet attachment device.

The probe assembly may further comprise the attachment device as described above for attaching the inlet to a chromatography device.

The inlet of the probe may be configured to be insertable into an orifice of the chromatography device and the inlet attachment device may be configured so as to releasably engage the orifice so as to releasably attach the probe to the chromatography device.

According to another aspect there is provided a chromatography device adapted to be connectable with an attachment device as described herein.

According to another aspect there is provided a chromatography device comprising apparatus as described herein.

According to another aspect there is provided a chromatography system comprising apparatus as described herein.

According to another aspect there is provided a mass and/or ion mobility spectrometer adapted to be connectable with an attachment device as described herein.

According to another aspect there is provided a mass and/or ion mobility spectrometer comprising apparatus as described herein.

According to another aspect there is provided a mass and/or ion mobility spectrometer system comprising apparatus as described herein.

The spectrometer may comprise one or more ion guides.

The spectrometer may comprise one or more ion mobility separation devices and/or one or more Field Asymmetric Ion Mobility Spectrometer devices.

The spectrometer may comprise one or more ion traps or one or more ion trapping regions.

The spectrometer may comprise a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser.

The spectrometer may comprise one or more energy analysers or electrostatic energy analysers.

The spectrometer may comprise one or more ion detectors.

The spectrometer may comprise one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter.

The spectrometer may comprise a device or ion gate for pulsing ions; and/or a device for converting a substantially continuous ion beam into a pulsed ion beam. The spectrometer may comprise a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser.

The spectrometer may comprise a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

The spectrometer may comprise a device arranged and adapted to supply an AC or RF voltage to the electrodes.

A chromatography detector may be provided, wherein the chromatography detector comprises either:

a destructive chromatography detector optionally selected from the group consisting of (i) a Flame Ionization Detector (FID); (ii) an aerosol-based detector or Nano Quantity Analyte Detector (NQAD); (iii) a Flame Photometric Detector (FPD); (iv) an Atomic-Emission Detector (AED); (v) a Nitrogen Phosphorus Detector (NPD); and (vi) an Evaporative Light Scattering Detector (ELSD); or a non-destructive chromatography detector optionally selected from the group consisting of: (i) a fixed or variable wavelength UV detector; (ii) a Thermal Conductivity Detector (TCD); (iii) a fluorescence detector; (iv) an Electron Capture Detector (ECD); (v) a conductivity monitor; (vi) a Photoionization Detector (PID); (vii) a Refractive Index Detector (RID); (viii) a radio flow detector; and (ix) a chiral detector.

The spectrometer may be operated in various modes of operation including a mass spectrometry ("MS") mode of operation; a tandem mass spectrometry ("MS/MS") mode of operation; a mode of operation in which parent or precursor ions are alternatively fragmented or reacted so as to produce fragment or product ions, and not fragmented or reacted or fragmented or reacted to a lesser degree; a Multiple Reaction Monitoring ("MRM") mode of operation; a Data Dependent Analysis ("DDA") mode of operation; a Data Independent Analysis ("DIA") mode of operation a Quantification mode of operation or an Ion Mobility Spectrometry ("IMS") mode of operation.

BRIEF DESCRIPTION OF THE DRAWINGS

Various embodiments will now be described, by way of example only, and with reference to the accompanying drawings in which.

DETAILED DESCRIPTION

Figure 1:
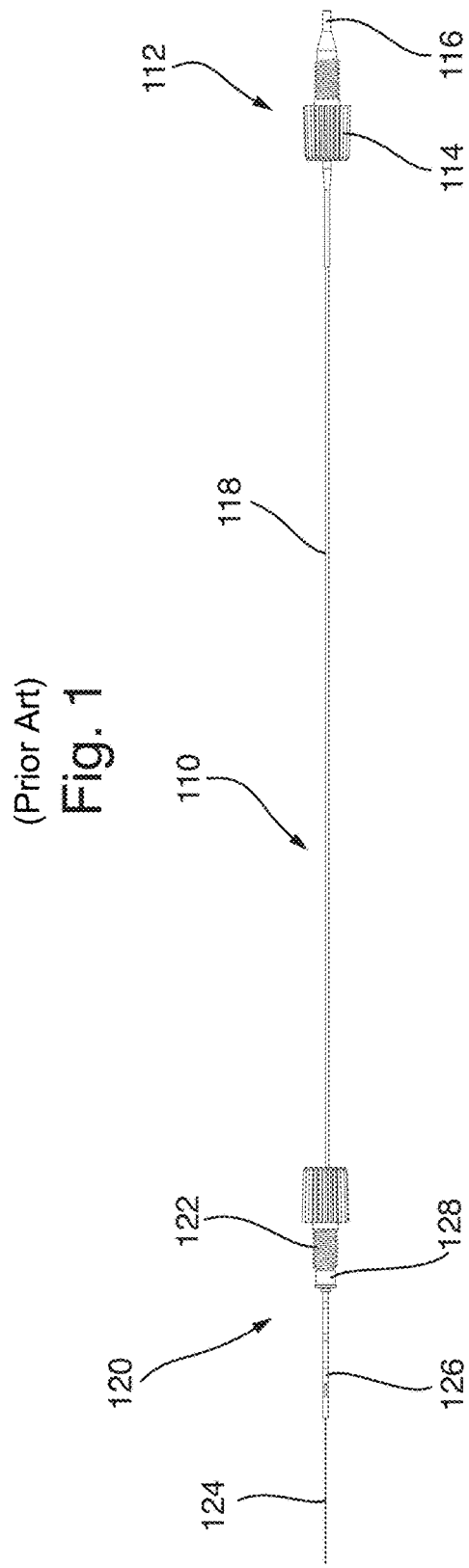
FIG. 1 shows schematically the probe assembly of GB-2520389.

FIG. 1 shows the probe assembly 110 of the Applicant's earlier application GB-2520389. The probe assembly 110 has an inlet end 112 having an inlet attachment fitting 114 that is configured for attaching the probe to a liquid chromatography device (not shown). A fluid inlet 116 is located at the inlet end 112 of the probe and is arranged to be insertable into a liquid chromatography output (not shown) such that the fluid inlet 116 receives eluent from the liquid chromatography instrument. A fluid line 118, e.g. in the form of a silica capillary, runs from the fluid inlet 116 to an outlet end 120 of the probe.

In use, the outlet end 120 is inserted into an ion source of a mass and/or ion mobility spectrometer (not shown), and is releasably secured in the spectrometer by the outlet attachment fitting 122. The attachment fitting comprises a screw threaded portion on its external surface that engages with and is screwed into a complementary screw thread on the spectrometer.

The fluid line 118 runs from the fluid inlet 116 at the inlet end 112 to a capillary 124, which is optionally electrically conductive, that forms a fluid outlet at the outlet end 120. The capillary 124 may be formed, for example, from steel or other suitable materials. The capillary 124 makes a joint (not shown) with the fluid line 118, which is optionally electrically insulating, at a location downstream of the outlet attachment fitting 122. This arrangement may ensure that only electrically insulated tubing extends out of the spectrometer from the attachment fitting 122, thereby reducing the risk of electrocution of the user. The capillary 124 receives eluent from the insulating fluid line 118 and delivers it into the spectrometer, when the outlet end 120 is attached to the spectrometer.

Figure 2:
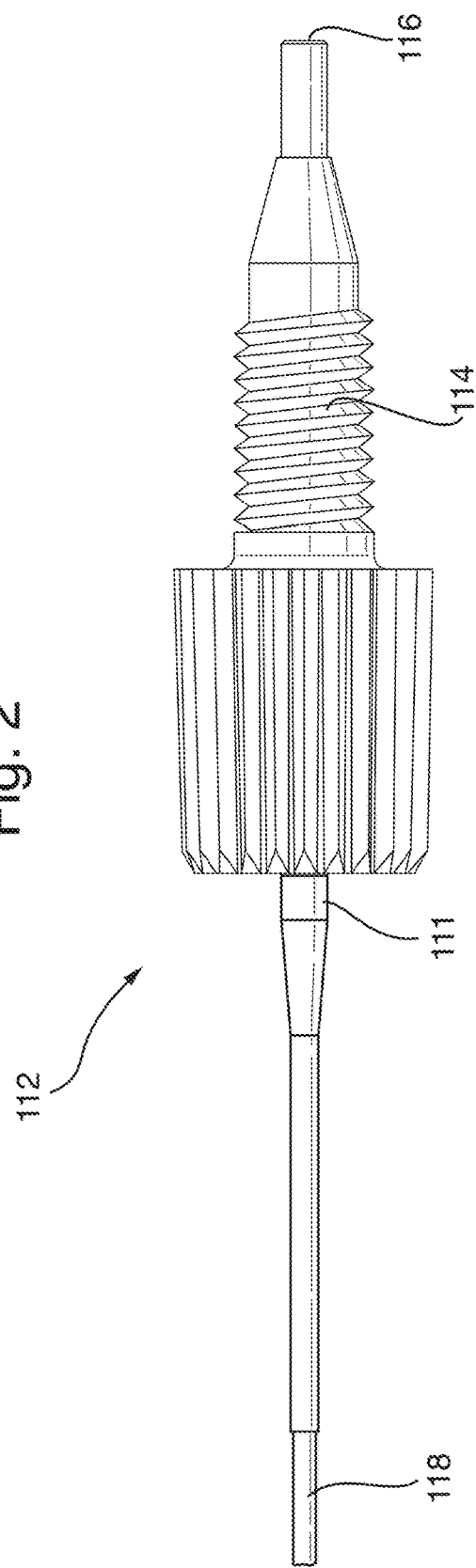
FIG. 2 shows schematically the inlet end of the probe assembly of FIG. 1 for being fitted into a liquid chromatography device.

FIG. 2 is a detailed view of the inlet end 112 of the probe assembly of FIG. 1, i.e. the end to be fitted into the liquid chromatography system. As described in relation to FIG. 1, the inlet end 112 has an inlet attachment fitting 114 for attaching the probe to a liquid chromatography device (not shown). In use, the inlet end 112 of the probe may be inserted into the liquid chromatography device and releasably secured therein. The attachment device may include a screw threaded portion and/or ratchet mechanism or other attachment fitting for engaging a complementary fitting or profile on the liquid chromatography device so as to releasably secure the probe in the liquid chromatography device.

FIGS. 3A, 3B, 3C, and 3D illustrate the process of forming the inlet end 112 of the probe assembly of FIG. 1.

Figure 3A:
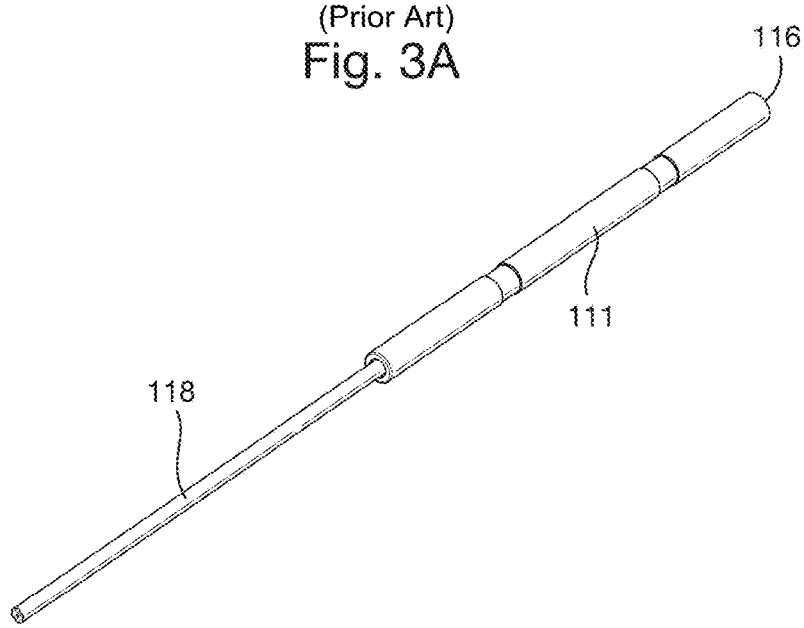
FIGS. 3A, 3B, 3C, and 3D show schematically the process of forming the inlet end of the probe assembly of FIG. 2.

As shown in FIG. 3A, an optional rigid or other member 111, e.g. in the form of a rigid tube, is crimped to the inlet end of a fluid line 118. The inlet end of the member 111 is arranged to be flush with the inlet end 116 of the fluid line 118. The member 111 may be formed, for example, from stainless steel or other suitable materials.

Figure 3B:
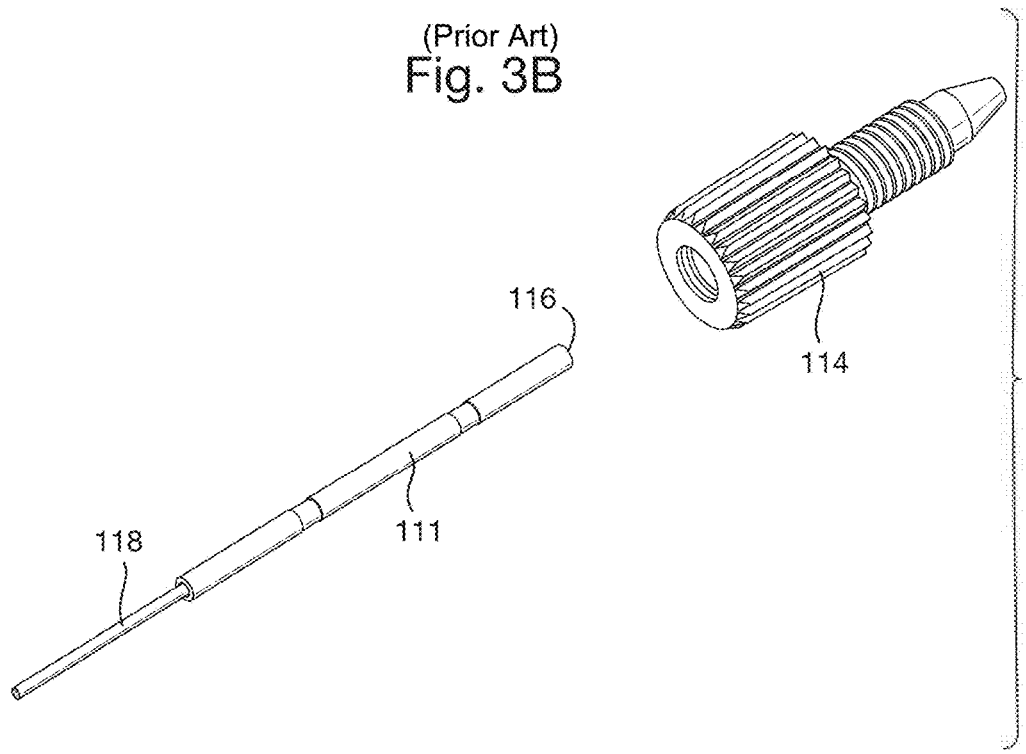
Figure 3C:
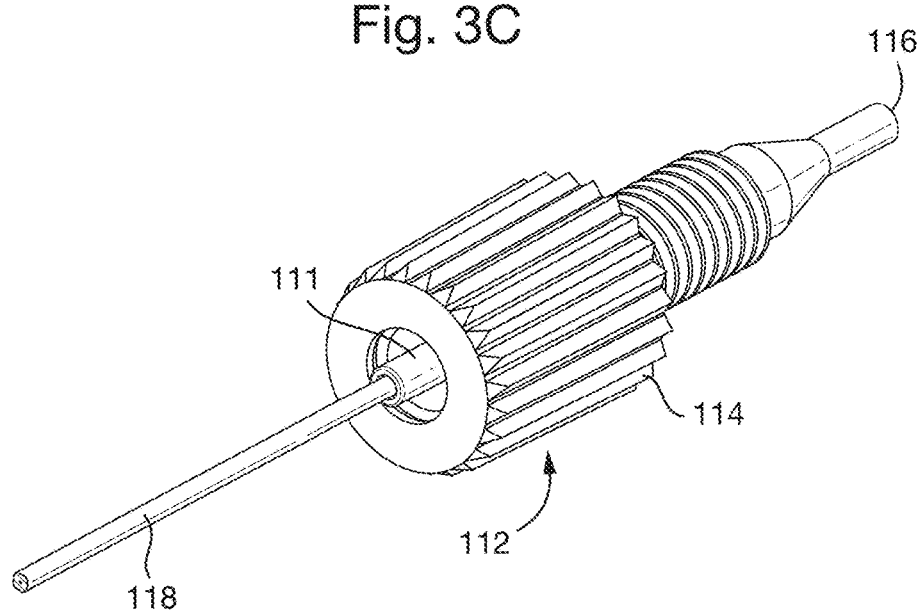

As shown in FIGS. 3B and 3C, an attachment fitting 114, e.g. in the form of a PEEK or other attachment fitting, is then attached to the member 111 (or directly to the fluid line 118), e.g. by pushing the (member 111 and the) fluid line 118 through a central orifice in the attachment fitting 114. A portion of the central orifice may have an inner diameter similar to or slightly smaller than the outer diameter of the member 111 (or fluid line 118), such that the attachment fitting 114 is gripped in place relative to the member 111 (and/or fluid line 118). The attachment fitting 114 may be gripped in place relative to the member 111 (and/or fluid line 118) only when the attachment fitting 114 is attached to its corresponding attachment device. Attaching the attachment fitting 114 to the rigid member 111 rather than directly to the silica capillary 118 (e.g. by crimping) can avoid deforming the silica capillary 118 (but this is not necessary).

Figure 3D:
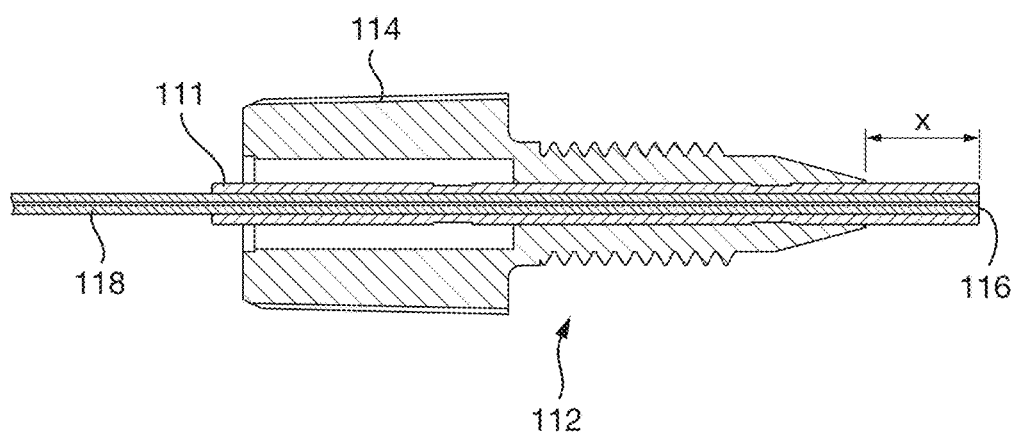

FIG. 3D shows a cross sectional view of the resulting inlet end 112 of the probe assembly.

The distance x between the inlet (upstream) end of the attachment fitting 114 and the fluid inlet 116 (upstream) end of the fluid line 118 should be selected in order to fit the outlet of the liquid chromatography device to which the probe inlet 112 is to be attached. However, attaching the attachment fitting 114 at the appropriate position (e.g. on the member 111) in order to achieve the desired distance x can be difficult, and may require more than one hand. The distance x may be set only when a user attaches the attachment fitting 114 to its corresponding attachment device, and may therefore be unsighted.

Furthermore, the attachment between the attachment fitting 114 and the rigid member 111, e.g. due to the member 111 and the fluid line 118 being pushed through the attachment fitting 114, can be poor, and may slip. In addition, once the attachment fitting 114 has been attached to the rigid member 111, it is difficult and inconvenient to then controllably alter the distance x, e.g. if it is desired to attached the fluid line to a different outlet device that requires a different distance x.

Figure 4:
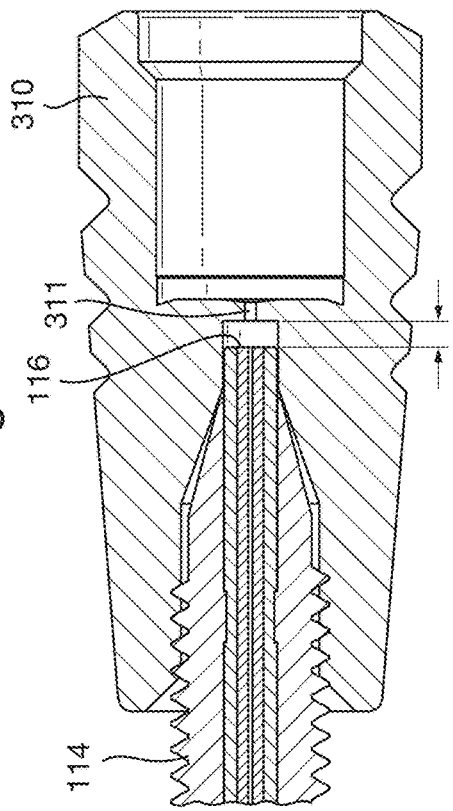
FIG. 4 shows schematically the inlet end of the probe assembly of FIG. 1 when incorrectly fitted in a liquid chromatography device outlet.

As illustrated by FIG. 4, where the distance x is incorrectly set for the particular outlet 310 of the liquid chromatography device to which the probe inlet 112 is to be attached, a dead volume can form between the inlet 116 of the fluid line 118 and the outlet bore 311 of the chromatography device. The formation of a dead volume can have a detrimental impact on the quality of the chromatography and overall the performance of the system, e.g. due to turbulent flow within the volume etc., e.g. may cause "band broadening". The likelihood of eluent leaking may also be increased.

A dead volume can also form where the inlet end 112 of the probe assembly is incorrectly attached to the liquid chromatography device outlet 310 and/or where the fluid line 114 slips relative to the attachment fitting 114. This can be more likely to occur when, for example, eluent is being eluted from the liquid chromatography device outlet 310, i.e. such that a pressure due to the eluent forces the inlet end 116 apart from the liquid chromatography device outlet bore 311.

According to various embodiments, an attachment device is provided for attaching a fluid line inlet to a fluid outlet (or for attaching a fluid line outlet to a fluid inlet) comprising an (inlet or outlet) attachment fitting, wherein the attachment fitting is attachable (or attached) to a fluid line such that the attachment fitting is moveable with respect to the fluid line, i.e. to which it is attached. Thus, the attachment member is preferably moveable relative to the fluid line when the attachment device is attached to the fluid line. Accordingly, the distance x between the inlet (upstream) end of the attachment fitting and the inlet (upstream) end of the fluid line is variable (or alternatively, the distance between the outlet (downstream) end of the attachment fitting and the outlet (downstream) end of the fluid line is variable).

According to various embodiments, the attachment fitting is attached to the fluid line such that when the attachment fitting is moved with respect to the fluid line (e.g. when the distance between the inlet (upstream) end of the attachment fitting and the inlet (upstream) end of the fluid line is varied), a spring or other elastic member is elastically deformed or stretched (or the elastic deformation or stretch of the spring or other elastic member is increased).

The attachment fitting may be configured such that in its "natural" equilibrium state, i.e. absent any applied external forces, the distance between the inlet (upstream) end of the attachment fitting and the inlet (upstream) end of the fluid line will take a first, e.g. equilibrium, value (or the distance between the outlet (downstream) end of the attachment fitting and the outlet (downstream) end of the fluid line will take a first, e.g. equilibrium, value).

When the distance (e.g. between the inlet (upstream) end of the attachment fitting and the inlet (upstream) end of the fluid line) is decreased from this first distance (e.g. due to a force on the fluid line and/or attachment fitting), the spring or other elastic member is elastically deformed or stretched (or the elastic deformation or stretch of the spring or other elastic member is increased), i.e. the spring or other elastic member is placed under tension or compression, such that the spring or other elastic member exerts a force on the fluid line and/or attachment fitting which acts in favour of returning the distance (e.g. between the inlet (upstream) end of the attachment fitting and the inlet (upstream) end of the fluid line) to the first (equilibrium) distance.

The first (equilibrium) distance may be set so as to be relatively long, i.e. larger than or equal to the corresponding distance within the attachment fitting of the liquid chromatography outlet or other fluid inlet or outlet to which the attachment device is to be fitted.

This will accordingly mean that when the attachment device is inserted into an outlet of a liquid chromatography device or other fluid inlet or outlet, then the inlet (or outlet) end of the fluid line will come into contact with the liquid chromatography device outlet bore (or other fluid inlet or outlet). As the attachment device is inserted further into the outlet (or inlet), i.e. as the attachment fitting is attached to the corresponding attachment fitting of the liquid chromatography outlet or other fluid inlet or outlet (e.g. by engaging screw threads of the attachment fitting with complementary screw threads or otherwise), the fluid line will be caused to move with respect to the attachment fitting (e.g. the distance x between the inlet (upstream) end of the attachment fitting and the inlet (upstream) end of the fluid line will be decreased from the first (equilibrium) distance), such that the spring or other elastic member will become deformed or stretched (or the elastic deformation or stretch of the spring or other elastic member will be increased), i.e. the spring or other elastic member will be placed under tension or compression.

Accordingly, as the attachment fitting is attached to (e.g. screwed to) the outlet (or inlet), then the spring or other elastic member will exert a force that acts to force and/or maintain the inlet (or outlet) end of the fluid line in contact with the liquid chromatography device outlet bore or other inlet or outlet. This prevents the formation of dead volumes, even if, for example, the attachment fitting is incorrectly attached to the outlet (or inlet), e.g. if the screw fitting is not completely screwed in. This also prevents undesired slipping of the attachment fitting relative to the fluid line. In addition, the attachment device and/or fluid line can be used in respect of multiple different inlet or outlet (e.g. liquid chromatography) devices.

It will be appreciated, therefore, that various embodiments provide an improved attachment device for coupling an inlet or outlet, e.g. of a fluid line, to an outlet, e.g. of a chromatography device, or an inlet, e.g. of a mass and/or ion mobility spectrometer.

Figure 5:
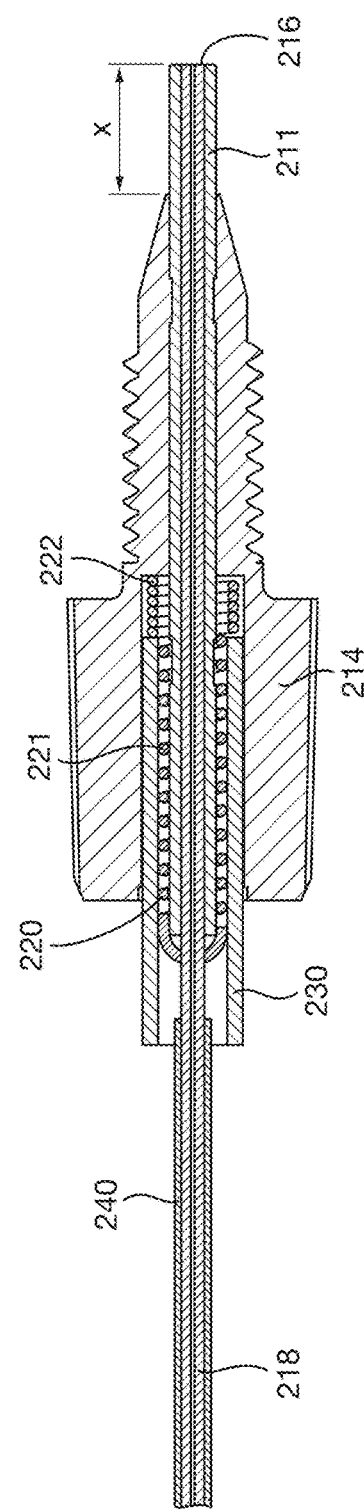
FIG. 5 shows a cross section view of an inlet attachment device when attached to the inlet of fluid line according to an embodiment.

FIG. 5 shows an attachment device for coupling a fluid inlet 216 of a fluid line 218 to an outlet, such as a liquid chromatography outlet 310 or other fluid outlet, in accordance with various embodiments. It will be understood that the attachment device according to various embodiments may also be used to couple a fluid outlet of a fluid line 218 to an inlet, such as an ion source inlet and/or mass and/or ion mobility spectrometer inlet. In this case the attachment device may be substantially as described below, mutatis mutandi.

The fluid inlet 216 of FIG. 5 is arranged to be insertable into a liquid chromatography or other liquid output (not shown) such that the fluid inlet 216 receives eluent from the liquid chromatography instrument or other outlet device. A fluid line 218, e.g. in the form of a silica capillary, runs from the fluid inlet 216 to an outlet end (not shown). Eluent received from the liquid chromatography instrument is transported through the fluid line 218 from the inlet end 216 to the outlet end (not shown).

The outlet end may comprise, for example, a capillary 124 of an ionisation probe assembly, e.g. as described above with respect to FIGS. 1 and 2, and as described further in GB-2520389. However, this is not necessary.

A first rigid member 211, e.g. in the form of a rigid tube, may be attached to the inlet end of the fluid line 218, e.g. by crimping the first rigid member 211 to the fluid line 218. The inlet end of the rigid member may be arranged to be flush with the inlet end 216 of the fluid line 218. The first rigid member 211 may be formed, for example, from stainless steel. Other suitable materials may be used.

The provision of a rigid member 111 can avoid deforming the fluid line (e.g. silica capillary 118), but this is not necessary. In some embodiments, the member 111 may be not (i.e. may be other than) rigid. In some embodiments, the member 111 is not provided.

As shown in FIG. 5, the attachment device is provided with an elastic member 220, such as a spring. The spring may be a tension spring, such as a helical tension spring. Other arrangements would be possible.

The helical spring may be arranged to at least partially surround the fluid line 218 and/or first rigid member 211, i.e. may be arranged coaxially with respect to the fluid line 218 and/or first rigid member 211, e.g. by passing the fluid line 218 and/or the first rigid member 211 through the helical spring.

An end or other portion of the elastic member 220 may be fixed with respect to the fluid line 218. In particular, an end or other portion of the elastic member 220 may be connected to the first rigid member 211. This may be achieved, for example, by hooking one end of the spring into an end (e.g. the downstream end) or other portion of the first rigid tube 211. Other arrangements would be possible.

An end or other portion of the elastic member 220 should be fixed with respect to the fluid line 218 (e.g. connected to the first rigid member 211) such that the elastic member 220 can be elastically deformed in the direction parallel to the longitudinal axis of the fluid line 218 and/or the first rigid member 211. For example, one end or other portion of the elastic member 220 may fixed with respect to the fluid line 218 (e.g. connected to the first rigid member 211) such that the elastic member 220 can be stretched in the direction parallel to the longitudinal axis of the fluid line 218 and/or the first rigid member 211 towards the inlet end 216 of the fluid line 218.

The attachment device is also provided with a second rigid member 230, e.g. in the form of a rigid tube. The second rigid member 230 may be formed, for example, from stainless steel. Other suitable materials may be used.

The second rigid member 230 may be arranged to at least partially surround the fluid line 218 and/or the first rigid member 211, i.e. may be arranged coaxially with respect to the fluid line 218 and/or the first rigid member 211. The second rigid member 230 may also be arranged to at least partially surround the elastic member 220, i.e. may be arranged coaxially with respect to the elastic member 220.

The second rigid member 230 is coupled to the elastic member 220, e.g. such that movement (in at least one direction) of the second rigid member 230 relative to the fluid line 218 and/or the first rigid member 211 (in the direction parallel to the longitudinal axis of the fluid line 218 and/or the first rigid member 211) causes the elastic member 220 to become elastically deformed (in the direction parallel to the longitudinal axis of the fluid line 218 and/or the first rigid member 211). In particular, the second rigid member 230 is coupled to the elastic member 220 such that movement of the second rigid member 230 relative to the fluid line 218 and/or the first rigid member 211 (in the direction parallel to the longitudinal axis of the fluid line 218 and/or the first rigid member 211) towards the inlet end 216 of the fluid line 218 causes the elastic member 220 to be stretched (in the direction parallel to the longitudinal axis of the fluid line 218 and/or the first rigid member 211) towards the inlet end 216 of the fluid line 218.

The second rigid member 230 may be coupled to the elastic member 220 in any suitable manner. For example, the elastic member 220 may comprise a first (helical) portion 221 having a first diameter and a second (helical) portion 222 having a second larger diameter. The first helical portion 221 may be arranged to be proximal to the end or other portion of the elastic member 220 that is fixed with respect to the fluid line 218 (e.g. to the end or other portion of the spring which is hooked into the downstream end of the first rigid tube 211), and the second (helical) portion 222 may be arranged to be distal to the end or other portion of the elastic member 220 that is fixed with respect to the fluid line 218 (i.e. may be arranged at or closer to the other end of the elastic member 220).

The first diameter may be less than or equal to the internal diameter of the second rigid tube 230 (such that the second rigid tube 230 can be slid over the first helical portion 221 of the elastic member 220), and the second diameter may be greater than the internal diameter of the second rigid tube 230 (such that the second rigid tube 230 cannot be slid over the second helical portion 222 of the elastic member 220).

As will be appreciated by those having skill in the art, this arrangement results in an "interference fit", such that movement of the second rigid member 230 relative to the fluid line 218 and/or the first rigid member 211 (in the direction parallel to the longitudinal axis of the fluid line 218 and/or the first rigid member 211) towards the inlet end 216 of the fluid line 218 causes the elastic member 220 to be stretched (in the direction parallel to the longitudinal axis of the fluid line 218 and/or the first rigid member 211) towards the inlet end 216 of the fluid line 218 as the second rigid member 230 pushes against the second helical portion 222 of the elastic member 220.

The first (helical) portion 221 may have a first pitch and the second (helical) portion 222 may have a second different (smaller) pitch.

The attachment device is also provided with an attachment fitting 214, e.g. in the form of a PEEK or other attachment fitting. Any suitable type of attachment fitting may be provided. For example, the attachment fitting may include a screw threaded portion and/or ratchet mechanism for engaging a complementary profile, e.g. on a liquid chromatography device so as to releasably secure the probe in the liquid chromatography device. Other types of attachment fitting that may be used include screw torque fittings, bayonet fittings, one or more clamps, one or more clips, etc.

The attachment fitting 214 is attached, e.g. fixedly attached, to the second rigid member 230, e.g. by crimping, gluing, or otherwise, the attachment fitting 214 to the second rigid member 230.

It would also be possible to attach the attachment fitting 214 (directly) to the elastic member 220. In this case, the second rigid member 230 may or may not be provided.

Accordingly, movement of the attachment fitting 214 relative to the fluid line 218 and/or the first rigid member 211 (in the direction parallel to the longitudinal axis of the fluid line 218 and/or the first rigid member 211) will (optionally) cause the second rigid member 230 to move, e.g. such that the elastic member 220 is deformed (in a corresponding manner to that discussed above with respect to movement of the second rigid member 230).

Movement of the attachment fitting 214 (and the attached second rigid member 230) relative to the fluid line 218 and/or the first rigid member 211 (in the direction parallel to the longitudinal axis of the fluid line 218 and/or the first rigid member 211) away from the inlet end 216 of the fluid line 218 is restricted due to the internal diameter of the inlet (upstream) end of the attachment fitting 214 being less than the (second) diameter of the second (helical) portion 222.

The attachment device 214 (and the attached second rigid member 230) may be able to rotate about the fluid line 218 (and the elastic member 220). This allows the user to rotate the attachment device 214 (and the attached second rigid member 230), e.g. so as to screw it or otherwise attach it to the liquid chromatography device or other outlet 310 so as to make a seal therewith, without twisting the fluid line 218 (and/or the elastic member 220), which would otherwise stress the tube.

Thus in various embodiments, the attachment member is rotatable about the fluid line (and the elastic member). The internal diameter of the attachment fitting 214 and/or the second rigid member 230 may be sized to allow the attachment fitting 214 (and the attached second rigid member 230) to be able to rotate about the fluid line 218 (and the elastic member 220), e.g. without twisting the fluid line 218 (and/or the elastic member 220). Similarly, the internal surface of the attachment fitting 214 and/or the second rigid member 230 may be finished (e.g. polished smooth, and without seams, ridges or notches, e.g. at the axial ends of the attachment fitting 214 and/or the second rigid member 230) to allow the attachment fitting 214 (and the attached second rigid member 230) to be able to rotate about the fluid line 218 (and the elastic member 220), e.g. without twisting the fluid line 218 (and/or the elastic member 220). The internal diameter of the second rigid tube 230 may be larger than the first diameter of the first (helical) portion 221 of the elastic member 220 (and the internal surface of the second rigid tube 230 may be finished) such that the second rigid tube 230 can rotate about the first (helical) portion 221 of the elastic member 220, e.g. without twisting the elastic member 220.

As will be understood by those having skill in the art, this arrangement results in an attachment device, wherein the attachment fitting 214 is attached to the fluid line 218 in such a way that the attachment fitting 214 is movable with respect to the fluid line 218 in the direction parallel to the longitudinal axis of the fluid line 218 and/or the first rigid member 211, and correspondingly such that the distance x between the inlet (upstream) end of the attachment fitting 214 and the inlet (upstream) end 216 of the fluid line 218 is variable.

The elastic member 220 may be arranged such that when it is under tension, it acts in favour of increasing the distance x between the inlet (upstream) end of the attachment fitting 214 and the inlet (upstream) end 216 of the fluid line 218.

When the attachment device is inserted into an outlet 310 of a liquid chromatography device or other fluid outlet, then the inlet end 216 of the fluid line 218 will come into contact with the liquid chromatography device outlet bore 311. As the attachment device is inserted further into the outlet 310, e.g. as the attachment fitting 214 is engaged with the corresponding attachment fitting of the outlet 310 (e.g. by engaging the screw threads of the attachment fitting with the complementary screw threads of the outlet 310 or otherwise), the fluid line 218 will be caused to move relative to the attachment fitting 214, and correspondingly the distance x between the inlet (upstream) end of the attachment fitting 214 and the inlet 216 (upstream) end of the fluid line 218 will be decreased from an equilibrium distance, such that the elastic member 220 will become deformed or stretched.

Accordingly, as the attachment fitting 214 is attached (e.g. screwed to) to the outlet 310, then the elastic member 220 will exert a force that acts to force the inlet end 216 of the fluid line 218 into contact with the liquid chromatography device outlet bore 311. This prevents the formation of dead volumes, even if, for example, the attachment fitting 214 is incorrectly attached to the outlet 310, e.g. if the screw fitting is not completely screwed in. This also prevents undesired slipping of the attachment fitting relative to the fluid line. In addition, the attachment device can be used in respect of multiple different outlet devices.

Figure 6:
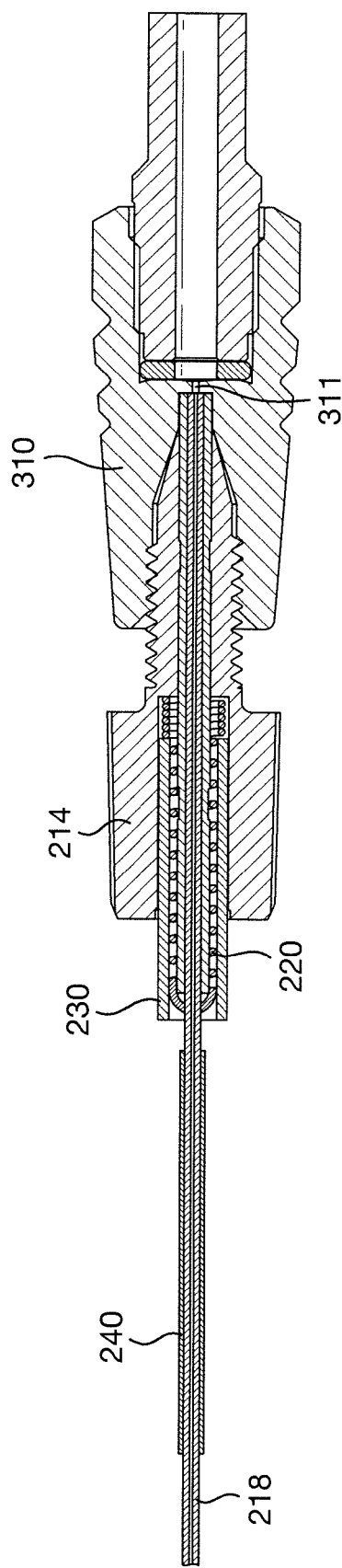
FIG. 6 shows a cross section view of the inlet attachment device of FIG. 5 when fitted into a liquid chromatography device outlet.

As illustrated by FIG. 6, the arrangement according to various embodiments beneficially prevents the formation of a dead volume when the attachment device is inserted into the chromatography device outlet 310 or other fluid outlet. In particular, as the attachment device is inserted into the outlet 310, the inlet end 216 of the fluid line 218 will butt up against the fluid bore 311 of the outlet so as to form a tight fluid connection. As the attachment device is inserted further, e.g. as the screw threads are tightened, the elastic member 220 will elastically deform, thereby forcing the inlet 216 against the outlet bore 311. This ensures that a tight fluid connection is achieved.

The elastic member 220 according to various embodiments is provided internally to the attachment fitting 214, i.e. the elastic member 220 beneficially does not add to the size or shape of the attachment fitting 214 or limit access to the attachment fitting 214.

Figure 7:
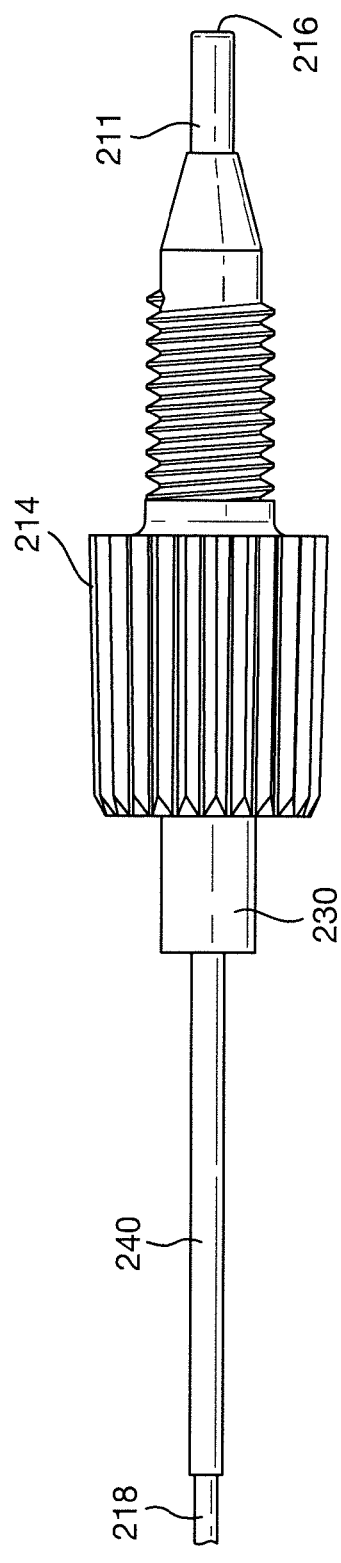
FIG. 7 shows schematically an external view of the inlet attachment device of FIG. 5.
Figure 8:
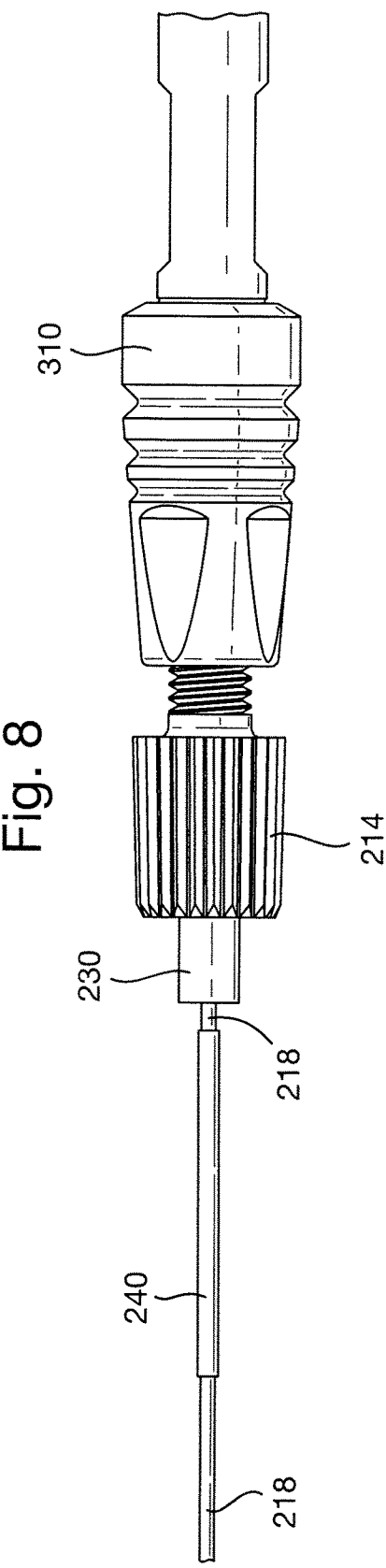
FIG. 8 shows schematically an external view of the inlet attachment device and the liquid chromatography device outlet of FIG. 6.

FIGS. 7 and 8 show external views of the attachment device shown in FIGS. 5 and 6.

A further tube member 240 may be provided on a portion of the fluid line 218 at least partially downstream from the attachment fitting 214. The tube member may comprise, for example, heat shrink that surrounds and is fixedly attached to the fluid line 218. The tube member may be marked with information such as a part number or other descriptive information.

As illustrated by FIG. 8, the tube member 240 may be arranged such that when the attachment device is correctly or fully attached to the chromatography device outlet 310 or other fluid outlet (e.g. such that the fluid line 218 is moved relative to the attachment fitting 214 as described above), then the tube member 240 will be at least partially or entirely exposed, i.e. not enclosed by the attachment fitting 214 and/or the second rigid member 230. In this case, a portion of the fluid line 218 upstream of the tube member 240 (that would otherwise be enclosed within the attachment fitting 214 and/or the second rigid member 230) may be exposed. This can serve as a visual indicator to show a user that the attachment device is correctly or fully connected to the chromatography device outlet 310 or other fluid outlet, e.g. to show that the inlet 216 has "bottomed out" in the outlet 310. This contrasts with the unsighted prior art approach described above.

It would additionally or alternatively be possible to mark the tube member 240 and/or the fluid line 218 with a marking that is exposed only when the attachment device is correctly or fully inserted into the chromatography device outlet 310 or other fluid outlet.

Although the above embodiments have been described primarily in terms of an inlet attachment device, the attachment device according to various embodiments may also be used to attach an outlet of a fluid line to a fluid inlet, e.g. of a mass and/or ion mobility spectrometer.

As described above, the fluid line 218 may be used to deliver eluent, e.g. from a chromatography device, to a mass and/or ion mobility spectrometer.

Although various embodiments described above reduce the possibility of a leak developing between the fluid line 218 and the chromatography outlet 310, it is still possible that if a user does not form the attachment correctly, a leak may develop. In this case, liquid may track along the fluid line 218, e.g. towards the mass and/or ion mobility spectrometer. That is, liquid may travel along the fluid line 218. In addition, other liquids may be accidentally spilled onto the fluid line, or may otherwise come into contact with the exterior of the fluid line 218, and may then track (travel) along the fluid line 218. The presence of liquid at the mass and/or ion mobility spectrometer and/or in other undesirable (and uncontrolled) locations can be hazardous and may give rise to the risk of electrical shock and/or poor performance.

According to various embodiments, a device 400 is provided for fitting to a fluid line 218, where the device 400 is configured such that when it is fitted to a fluid line 218, the device 400 prevents, e.g. blocks, most or all liquid from tracking (travelling) along the fluid line 218. The device 400 may be configured to cause intercepted liquid to drip from or otherwise leave the device 400 and/or the fluid line 218.

Figure 9:
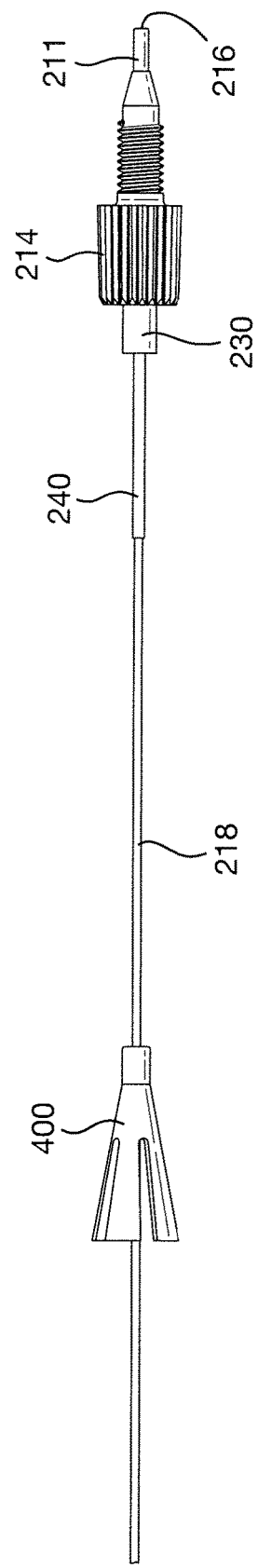
FIG. 9 shows schematically an inlet attachment device attached to the inlet of fluid line together with a device that prevents liquid tracking along the fluid line.

As shown in FIG. 9, the device 400 may be fitted to a fluid line 218, e.g. a fluid line which is to be connected to a liquid chromatography device (as described above) or otherwise. The device 400 is arranged such that most or all liquid that tracks along the fluid line 218, e.g. due to a leak at the attachment fitting 214, cannot continue beyond the device 400, i.e. most or all of the fluid cannot reach the portion of the fluid line 218 that is downstream from the device 400.

The device 400 should surround the fluid line 218, i.e. such that liquid tracking along any surface of the fluid line 218 may be intercepted by the device 400.

The device 400 may be beneficially fitted to the fluid line 218 as close as possible to any potential leak source, such as the attachment fitting 214.

The device 400 may be fitted to a portion of fluid line 218 along which it is likely that fluid will flow, such as a sloping portion of fluid line or otherwise.

The position of the device 400 may be selected such that intercepted liquid will drip or otherwise fall onto a selected, e.g. non-hazardous, surface or other location. For example, the device may be positioned above a liquid collector or drain.

The device may be fitted to the fluid line 218 by threading the fluid line 218 through central bore in the device 400. Additionally or alternatively, the device 400 may be provided with a slot, and may be fitted to the fluid line 218 by passing the fluid line through the slot and/or clipping or snapping the device 400 onto the fluid line 218.

The device may be fixed to the fluid line 218, e.g. by means of crimping, gluing, heat shrink, mechanical fasteners, etc., or may be arranged to move freely along the fluid line 218.

Figure 10:
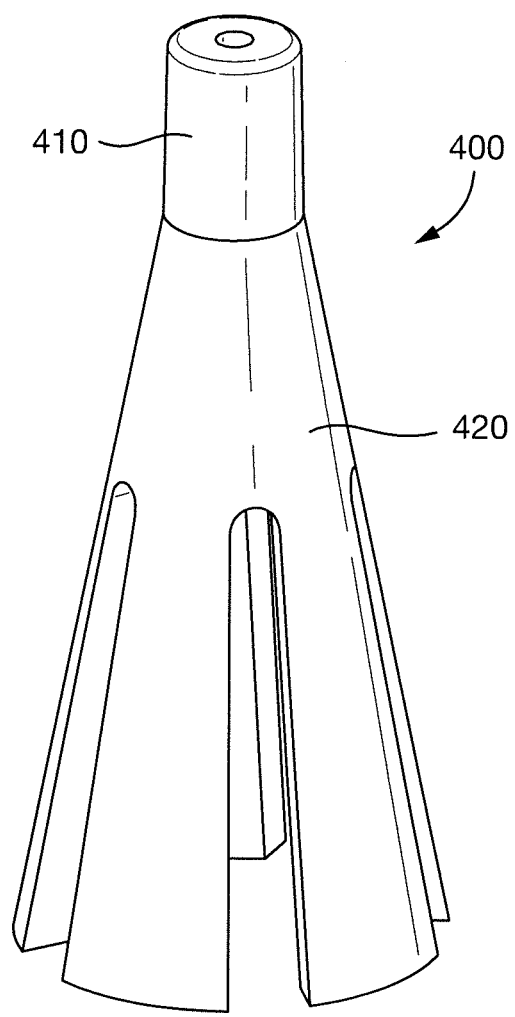
FIG. 10 shows a detailed view of the device for preventing liquid tracking of FIG. 9.

FIG. 10 shows a detailed view of the device 400. As shown in FIG. 10, the device 400 may comprise a first portion 410, and a conical portion 420, e.g. a truncated conical portion.

The first portion 410 may comprise an inner bore or hole. In use, the device 400 may be fitted to a fluid line 218 by passing the fluid line 218 through the bore or hole.

The first portion 410 may comprise a tubular portion. The tubular portion 410 may comprise a tube or hollow cylinder having an inner bore. Other arrangements would be possible.

An internal diameter of the first portion 410 bore or hole may be equal to or slightly larger than the outer diameter of the fluid line 218 to which the device 400 is to be fitted. The internal diameter (and the axial length of the first portion 410) may be selected such that when fitted to the fluid line 218, the first portion 410 remains substantially coaxially aligned with the fluid line 218. That is, the internal diameter (and the axial length of the tube 410) may be selected such that the device 400 does not "droop" when fitted to the fluid line 218. In particular, the internal diameter (and the axial length of the tube 410) may be selected such that when fitted to the fluid line 218, the conical portion 420 does not touch (is space apart from) the fluid line 420 (at least when the fluid line 420 is substantially straight).

The internal diameter may be selected such that most or all liquid that tracks along any surface of the fluid line 218 is intercepted by the device 400, i.e. such that the fluid does not continue beyond (downstream of) the device 400.

The internal diameter may be selected such that the device 400 cannot move and/or rotate relative to the fluid line 218 to which it is fitted. Alternatively, the internal diameter may be selected such that the device 400 can move and/or rotate relative to the fluid line 218 to which it is fitted. Rotation of the device 400 may prevent liquid building up on portions of the device 400 that are positioned above the fluid line 218, e.g. since any such build-up will instead cause the device 400 to rotate relative to the fluid line 218, e.g. such that the liquid build-up will then be positioned beneath the fluid line 218. This in turn prevents liquid from dripping onto the fluid line 218 from the device 400, and therefore prevents liquid tracking (travelling) beyond (downstream of) the device 400.

The conical portion 420 may have the form of a hollow truncated cone. The truncated conical portion 420 may be connected to the first portion 410, e.g. at its truncated end. The truncated conical portion 420 may be connected to the first portion 410 so as to be coaxially aligned with the first (e.g. tube) portion 410. The truncated conical portion 420 may be formed integrally with the first portion 410. The diameter of the truncated conical portion 420 may increase (e.g. linearly) from the point at which the truncated conical portion 420 is connected to the first portion 410 to the (downstream) end of the conical portion 420.

In use, the first portion 410 is positioned relatively close to any likely leak source (such as the attachment fitting 214), while the conical portion 420 is positioned relatively distant from the potential leak source.

The arrangement according to various embodiments causes liquid intercepted by the device 400 to drip or otherwise fall from the device 400.

According to various further embodiments, the conical portion 420 may comprise one or more (open ended) slots or other indentations, e.g. one or more (open ended) slots or other indentations may be formed in the walls of the hollow truncated cone. The slots may be parallel to the central axis of the device 400. The width and/or length of the slot(s) may be selected as desired.

This arrangement acts to cause liquid to drip from or otherwise leave the device 400.

In addition, the provision of slots in the walls of the hollow truncated cone allows the device 400 to be collapsed, e.g. such that the device 400 can be passed through relatively small apertures. Accordingly, the length, width, shape, and/or number, etc., of the one or more slots may be selected such that the device 400 can be collapsed in order to fit through an particular aperture, i.e. an aperture through which it is desired to pass the device 400. The device 400 may be configured so as to be collapsible to a size that is the same as or similar to the attachment fitting 214, i.e. so that the device 400 will be able to fit through the same apertures through which the attachment fitting 214 can be passed.

In particular, the length of the one or more slots may be selected such that the diameter of the conical portion 420 at the point at which the one or more slots end is less than the diameter of a particular aperture, i.e. an aperture through which it is desired to pass the device 400.

The device 400 may have rotational symmetry, e.g. about its central axis. Where, as discussed above, the device 400 is arranged to be freely rotatable around the fluid line 218, this means that if liquid builds up asymmetrically on the device 400, the device 400 can rotate (under the influence of gravity) such that the liquid build-up is positioned beneath the fluid line 218 and will not then drip or otherwise fall onto the fluid line 218.

The device 400 may have a range of variants suited to different applications. For example, the device 400 may be provided with different bore sizes, and/or cross-sectional shapes for the fluid line in question, different variations of the various lengths, different configurations for the first (e.g. tube) portions, conical portions, and/or slots that e.g. may be optimised to cause different liquids (having different viscosities, etc.) to drip or otherwise fall from the device 400, and so on.

Although the above embodiments have been described primarily in terms of a device 400 for fitting to a fluid line 218, e.g. of a probe assembly that is to be connected to a liquid chromatography device, the device 400 may find applications in a variety of other situations. In general, the device 400 may be used wherever it is desired to prevent liquid from tracking (travelling) along a member such as a line, wire, cable, tube, pipe, and the like. For example, the device 400 may be used to prevent liquid, e.g. rain water, tracking (traveling) along an exposed wire, cable or other member. Other uses will be apparent to the skilled person.

Although the present invention has been described with reference to preferred embodiments, it will be understood by those skilled in the art that various changes in form and detail may be made without departing from the scope of the invention as set forth in the accompanying claims.

The invention claimed is:

1. An attachment device for releasably attaching a fluid line to a fluid inlet or outlet, the device comprising:
   an attachment member for releasably engaging a fluid inlet or outlet;
   an elastic member coupled to the attachment member; and
   a rigid member coupled to the elastic member;
   wherein the attachment device is attachable to a fluid line such that the attachment member is moveable relative to the fluid line and such that movement of the attachment member relative to the fluid line causes the elastic member to be elastically stretched;
   wherein the elastic member comprises a first portion having a first diameter and a second portion having a second larger diameter;
   wherein the rigid member partially surrounds the elastic member; and
   wherein the first diameter is less than or equal to an internal diameter of the rigid member, and the second diameter is greater than the internal diameter of the rigid member such that movement of the rigid member relative to the fluid line causes the elastic member to be elastically stretched by the rigid member pushing against the second portion of the elastic member.

2. The attachment device as claimed in claim 1, wherein the attachment device is attachable to a fluid line such that the distance between the attachment member and an outlet and/or inlet of the fluid line is variable and such that decreasing the distance causes the elastic member to be elastically stretched.

3. The attachment device as claimed in claim 1, wherein the elastic member comprises a helical tension spring.

4. The attachment device as claimed in claim 1, wherein the attachment device is attachable to a fluid line such that an end or other portion of the elastic member is fixed with respect to the fluid line.

5. The attachment device as claimed in claim 1, wherein the fluid line comprises a second rigid member attached to the outlet and/or inlet of the fluid line.

6. The attachment device as claimed in claim 5, wherein the attachment device is attachable to a fluid line such that an end or other portion of the elastic member is connected to the second rigid member by the end or other portion of the elastic member being hooked into an end or other portion of the second rigid member.

7. The attachment device as claimed in claim 1, wherein the attachment member is attached to the rigid member.

8. An apparatus for releasably attaching a fluid line to a fluid inlet or outlet, the apparatus comprising:
   an attachment device as claimed in claim 1; and
   a fluid line;
   wherein the attachment device is attached to the fluid line such that the attachment member is moveable relative to the fluid line and such that movement of the attachment member relative to the fluid line causes the elastic member to be elastically stretched.

9. The apparatus as claimed in claim 8, wherein the fluid line comprises a device or marking positioned on the fluid line such that at least a portion of the device or marking is exposed when the attachment device is correctly or fully releasably attached to the fluid inlet or outlet.

10. The apparatus as claimed in claim 8, further comprising:
    a fluid inlet or outlet, wherein the attachment device is releasably attachable to the fluid inlet or outlet so as to releasably attach the fluid line to the fluid inlet or outlet.

11. The apparatus as claimed in claim 8, further comprising:
    a device fitted to the fluid line, wherein the device is configured to intercept liquid on the fluid line and to cause at least some of the intercepted liquid to drop or otherwise fall from the device and/or from the fluid line.

12. The apparatus as claimed in claim 11, where the device comprises a first portion and a conical portion.

13. A method comprising:
    providing the apparatus as claimed in claim 8;
    using the attachment device to releasably attach the fluid line to a fluid inlet or outlet; and
    delivering fluid from the fluid outlet to the fluid line or delivering fluid from the fluid line to the fluid inlet.

* * * * *